United States Patent
Toussaint et al.

(10) Patent No.: US 12,274,547 B2
(45) Date of Patent: Apr. 15, 2025

(54) OPTICAL DETERMINATION OF A CARDIOVASCULAR VARIABILITY PARAMETER INDEPENDENT OF SKIN CONTRIBUTIONS

(71) Applicant: BROWN UNIVERSITY, Providence, RI (US)

(72) Inventors: Kimani Toussaint, Providence, RI (US); Rutendo Jakachira, Providence, RI (US); Mbaye Diouf, Providence, RI (US); Joshua Burrow, Providence, RI (US); Zixi Lin, Providence, RI (US)

(73) Assignee: BROWN UNIVERSITY, Providence, RI (US)

( * ) Notice: Subject to any disclaimer, the term of this patent is extended or adjusted under 35 U.S.C. 154(b) by 0 days.

(21) Appl. No.: 18/681,759

(22) PCT Filed: Aug. 11, 2022

(86) PCT No.: PCT/US2022/040020
§ 371 (c)(1),
(2) Date: Feb. 6, 2024

(87) PCT Pub. No.: WO2023/018846
PCT Pub. Date: Feb. 16, 2023

(65) Prior Publication Data
US 2025/0000398 A1    Jan. 2, 2025

Related U.S. Application Data

(60) Provisional application No. 63/231,973, filed on Aug. 11, 2021, provisional application No. 63/353,566, filed on Jun. 18, 2022.

(51) Int. Cl.
*A61B 5/1455* (2006.01)
*A61B 5/00* (2006.01)
(Continued)

(52) U.S. Cl.
CPC ...... *A61B 5/14552* (2013.01); *A61B 5/14558* (2013.01); *A61B 5/7275* (2013.01);
(Continued)

(58) Field of Classification Search
CPC .......... A61B 56/1455; A61B 56/14552; A61B 56/14558
See application file for complete search history.

(56) References Cited

U.S. PATENT DOCUMENTS

| 5,687,721 A | 11/1997 | Kuhls |
| 5,954,658 A | 9/1999 | Gorti |

(Continued)

OTHER PUBLICATIONS

PCT Search Report and Written Opinion for corresponding International Application Serial No. PCT/US2022/040020 mailed Oct. 31, 2022, 18 pages.

*Primary Examiner* — Marjan Fardanesh
(74) *Attorney, Agent, or Firm* — Tarolli, Sunhdeim, Covell & Tummino LLP

(57) ABSTRACT

A cardiovascular variability parameter can be detected independent of the relative absorption contribution of melanin in biological tissue. A light source and a polarization shaping device can illuminate a biological tissue with a polarized light having an inhomogeneous optical polarization wavefront. A polarization analyzer can receive the polarized light after it has interacted with the biological tissue and output a first and second polarization state. A detection device can have a light detector for detecting the first and second polarization state and at least a processor for detecting data related to the first and second polarization states, determining relative absorptions contributions of superficial and deep components of the biological tissue based on the first and second polarization states, and determining the cardiovascular variability parameter based on the relative absorption contributions of the superficial and deep components.

20 Claims, 11 Drawing Sheets

(51) Int. Cl.
  *A61B 5/02* (2006.01)
  *A61B 5/021* (2006.01)
  *A61B 5/024* (2006.01)
  *A61B 5/026* (2006.01)
  *A61B 5/08* (2006.01)

(52) U.S. Cl.
  CPC ....... *A61B 5/02007* (2013.01); *A61B 5/02028* (2013.01); *A61B 5/021* (2013.01); *A61B 5/02444* (2013.01); *A61B 5/0261* (2013.01); *A61B 5/0803* (2013.01); *A61B 5/0816* (2013.01); *A61B 2560/0443* (2013.01); *A61B 2560/0462* (2013.01)

(56) References Cited

U.S. PATENT DOCUMENTS

| | | |
|---|---|---|
| 2007/0016080 A1 | 1/2007 | Alfano et al. |
| 2019/0223730 A1 | 7/2019 | Pierro et al. |
| 2021/0059533 A1 | 3/2021 | Patwardhan |

-Prior Art-

OPTICAL DETERMINATION OF A CARDIOVASCULAR VARIABILITY PARAMETER INDEPENDENT OF SKIN CONTRIBUTIONS

CROSS-REFERENCE TO RELATED APPLICATIONS

This application claims the benefit of U.S. Provisional Application Ser. No. 63/231,973, filed 11 Aug. 2021, entitled "A NOVEL OPTICAL METHOD FOR ACCURATE BLOOD OXYGENATION MEASUREMENTS INDEPENDENT OF SKIN TONE AND OTHER SKIN CONTRIBUTIONS" and U.S. Provisional Application Ser. No. 63/353,566, filed 18 Jun. 2022, entitled "A NOVEL OPTICAL METHOD FOR ACCURATE BLOOD OXYGENATION MEASUREMENTS INDEPENDENT OF SKIN TONE AND OTHER SKIN CONTRIBUTIONS". The entirety of these applications is incorporated by reference for all purposes.

GOVERNMENT FUNDING

This invention was made with government support under a Multidisciplinary University Research Initiative (MURI) grant from the Office of Naval Research grant number N00014-20-1-2789. The government of the United States has certain rights in the invention.

TECHNICAL FIELD

The present disclosure relates generally to optical measurements of one or more cardiovascular variability parameters and, more specifically, to systems and methods of optically determining one or more cardiovascular variability parameters independent of skin contributions (e.g., skin tone).

BACKGROUND

Photoplethysmography (PPG) can be used in a variety of commercially available medical devices as a simple, low cost, and non-invasive way to monitor one or more cardiovascular variability parameters, such as pulse oximetry for measuring estimated oxygen saturation ($SpO_2$). For example, a conventional pulse oximeter with a PPG utilizes two wavelengths of light (e.g., approximately 660 nm and 940 nm) to differentiate the absorption of chromophores in oxyhemoglobin ($HbO_2$) and deoxyhemoglobin (Hb).

While the two wavelengths of light do provide a ratiometric measure of $HbO_2$ concentration to the amount total amount of Hb, which is then used to estimate $SpO_2$, chromophores like melanin also absorb light at these wavelengths and can distort calculations. Melanin, the chromophore responsible for pigmentation of parts of the body, including skin, hair, and eyes, absorbs light across the light spectrum and by differing amounts for different wavelengths. Conventional pulse oximetry fails to consider the wavelength dependence of melanin, which can vary significantly from person-to-person. Many pulse oximeters have been calibrated for lighter pigmented skin types. The results of these devices are often inaccurate for darker skinned patients, which can lead to late recognition of hypoxia or other serious medical conditions.

SUMMARY

The present disclosure illustrates the optical determination of one or more cardiovascular variability parameters, such as pulse oximetry, independent of the effects of melanin. Accordingly, one or more cardiovascular variability parameters can be optically determined independent of skin contributions, such as skin tone.

One aspect of the present disclosure is a system for determining a cardiovascular variability parameter independent of the relative absorption contribution of melanin. The system includes at least a light source, a polarization shaping device and a polarization analyzer. The light source is configured to generate a light to illuminate a biological tissue of a patient. The polarization shaping device is configured to polarize the light to have an inhomogeneous optical polarization wavefront creating polarized light. The polarized light is configured to interact with the biological tissue of the patient as reflectance and/or transmission. The polarization analyzer is configured to: receive interacted polarized light comprising the polarized light reflected after the polarized light interacts with the biological tissue of the patient; and output at least a first polarization state and a second polarization state of the interacted polarized light. A portion of the polarization analyzer is oriented at a first angle relative to the interacted polarized light to output the first polarization state and another portion of the polarization analyzer is oriented at a second angle relative to the interacted polarized light to output the second polarization state. The system also includes a detection device comprising a light detector and at least a processor. The light detector is configured to detect the first and second polarization states of the interacted polarized light output by the polarization analyzer. The processor is configured to execute instructions to: detect data related to the first polarization state of the interacted polarized light and data related to the second polarization state of the interacted polarized light; determine relative absorption contributions of a superficial component and a deep component of the biological tissue of the patient based on the data related to the first polarization state of the interacted polarized light and the data related to the second polarization state of the interacted polarized light; and determine a cardiovascular variability parameter of the patient based on the relative absorption contributions of the superficial component and the deep component, wherein the determination is independent of an absorption effect of melanin in the biological tissue.

Another aspect of the present disclosure is a method for determining a cardiovascular variability parameter independent of the relative absorption contribution of melanin. The method comprising: receiving, by a detection device comprising at least a processor and a light detector, data related to a first polarization state and a second polarization state of an interacted polarized light, wherein the interacted polarized light comprises polarized light reflected after a polarized light interacts with biological tissue of a patient, wherein the detection device is part of a system that further comprises: a light source configured to generate light to illuminate a biological tissue of a patient; a polarization shaping device configured to polarize the light to have an inhomogeneous optical polarization wavefront, wherein the polarized light is configured to interact with the biological tissue of the patient wherein the interaction is reflectance or reflectance and transmission; and a polarization analyzer configured to receive the interacted polarized light and output at least the first polarization state and the second polarization state of the interacted polarized light, wherein a portion of the polarization analyzer is oriented at a first angle relative to the interacted polarized light to output the first polarization state and another portion of the polarization analyzer is oriented at a second angle relative to the interacted polarized light to output the second polarization state, wherein the light detector of the detection device is configured to detect the first and second polarization states of the light output by the polarization analyzer; determining, by the detection device, relative absorption contributions of a superficial component and a deep component of the biological tissue of the patient based on the data related to the first polarization state and the data related to the second polarization state; and determining, by the detection device, a cardiovascular variability parameter of the patient based on the relative absorption contributions of the superficial component and the deep component, wherein the determination is independent of an absorption effect of melanin in the biological tissue.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

1. Definitions

Figure 1:
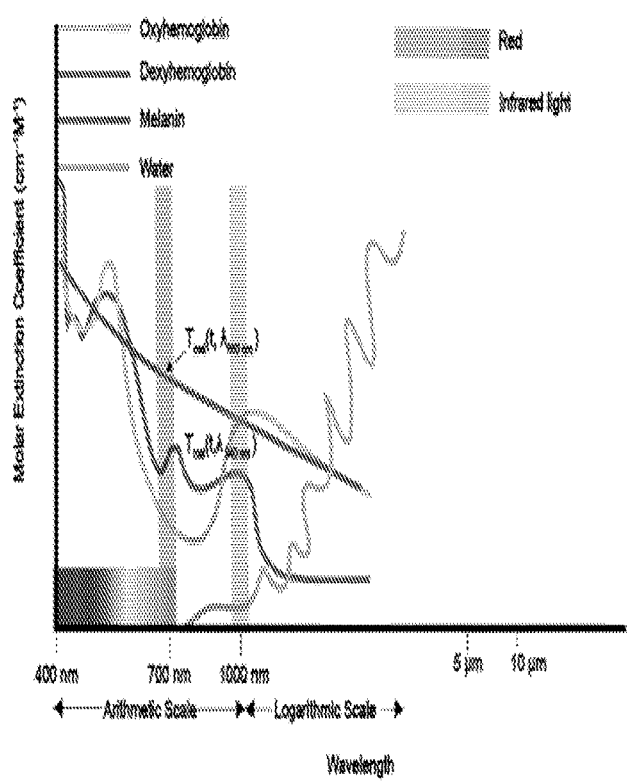
FIG. 1 is an example of a conventional pulse oximeter approach laid over an absorption spectra for oxyhemoglobin, deoxyhemoglobin, melanin, and water.

Unless otherwise defined, all technical terms used herein have the same meaning as commonly understood by one of ordinary skill in the art to which the present disclosure pertains.

As used herein, the singular forms "a," "an," and "the" can also include the plural forms, unless the context clearly indicates otherwise.

As used herein, the terms "comprises" and/or "comprising," can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

As used herein, the terms "first," "second," etc. should not limit the elements being described by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

As used herein, the term "biological tissue" refers to one or more collections of interconnected cells that perform one or more functions within a patient. These collections of interconnected cells can include skin, fat, muscle, bone, and/or hair. Not limiting examples of biological tissue can include, but are not limited to, the entire body, a portion of the entire body, one or more organs of the body, or the like.

As used herein, the term "chromophore" refers to an atom or group of atoms whose presence is responsible for color. One example chromophore in a patient's body is melanin.

As used herein, the term "melanin" refers to a chromophore in a patient's body that produces hair, eye, and skin pigmentation. The more melanin produced, the darker coloration of the hair, eyes, and skin. The darker coloration of the hair, skin, and/or eyes, the more melanin produced by the patient.

As used herein, the term "cardiovascular variability parameter" refers to a parameter related to blood flow and/or transportation of substances in blood. Examples of cardiovascular variability parameters include heart rate, respiratory rate, estimated oxygen saturation ($SpO_2$), tissue oxygenation ($StO_2$), arterial blood pressure, blood vessel stiffness, microvascular blood flow, tissue viability, vasomotor function, thermoregulation, etc. Cardiovascular variability parameters also can be used for cardiovascular assessments, assessing cardiology, vascular assessments, assessing orthostasis, assessing neurology, or the like.

As used herein, "photoplethysmography" also referred to as a "PPG" refers to a simple, low cost, and non-invasive technique used in a variety of commercially available medical devices for optical-physiological monitoring of one or more cardiovascular variability parameters. Generally, a PPG can include at least one light source for illuminating skin of a patient and a detector for measuring light signals transmitted and/or reflected from the skin of the patient.

As used herein, a "light source" refers to a device whose primary function is to produce visible or near-visible radiant energy (e.g., light) for general illumination or specialty applications. A light source can include one or more light emitting diodes, one or more super luminescent diodes, one or more incoherent lamp (e.g., xenon, tungsten, halogen, etc.), one or more continuous wave laser, one or more femtosecond laser, or the like.

As used herein, a "light detector" refers to a device or circuit that can detect light incident on it. Examples of light detectors can include one or more CCD cameras, one or more CMOS cameras, one or more photodiodes, one or more photoconductors, one or more polarimeters, one or more photo- and/or thermal-detectors, one or more PMT balanced detectors, or the like.

As used herein, the term "polarize" refers to restricting vibrations of a light wave wholly or partially to one direction.

As used herein, the term "polarizer" refers to an optical device that can convert a beam of unpolarized light into one that is polarized into a polarization state. A polarization shaping device and a polarization analyzer can each include one or more polarizers.

As used herein, the term "polarization state" refers to a state of a light wave that has been polarized. There are various kinds of polarization states of light, including but not limited to, linear, circular, elliptical, radial, and azimuthal. Light can include one or more than one polarization state at a time. For example, light can be polarized to have an inhomogeneous optical polarization wavefront.

As used herein, the term "patient" refers to any warm-blooded organism from which a tissue sample can be taken, including, but not limited to, a human being, a pig, a rat, a mouse, a dog, a cat, a goat, a sheep, a horse, a monkey, an ape, a rabbit, a cow, etc. The terms patient and subject can be used interchangeably.

II. Overview

Many commercially available medical devices can use photoplethysmography (PPG) to monitor one or more cardiovascular variability parameters. For example, a pulse oximeter can include a PPG for estimating blood oxygen saturation ($SpO_2$). Such a traditional pulse oximeter can utilize two lights at different wavelengths to differentiate the absorption of chromophores in oxyhemoglobin ($HbO_2$) and deoxyhemoglobin (Hb). Traditionally, one wavelength of light was chosen in the red band and the other wavelength of light was chosen in the infrared band as there is maximal difference in light absorption by $HbO_2$ and Hb chromophores at these wavelengths (shown graphically in FIG. 1). Data recorded at these wavelengths can be used to provide a radiometric measure of $HbO_2$ and Hb which can then be used to estimate $SpO_2$. However, the wavelengths chosen do not account for the effect of melanin at different wavelengths, which varies significantly based on complexion. Traditional pulse oximeters, and other devices that use PPGs, have to be calibrated for a specific melanin concentration and this calibration is traditionally done with a light skin tone (that includes minimal melanin effects). However, because such devices are used across many patients and only calibrated once so these devices are not accurate across a range of skin tones, especially darker skin tones with greater melanin effects. Accordingly, the results of these devices are often inaccurate for darker skinned patients, which can lead to late recognition of hypoxia or other serious medical conditions. Such inaccurate results for darker skinned patients cause serious problems. In fact, traditional pulse oximeters have been found to be inaccurate in three times as many cases for African American patients as for white patients. Inaccurate diagnoses can cause patients to receive improper medical care, or no medical care when it is needed, and can lead to distrust of the entire medical community.

Figure 2:
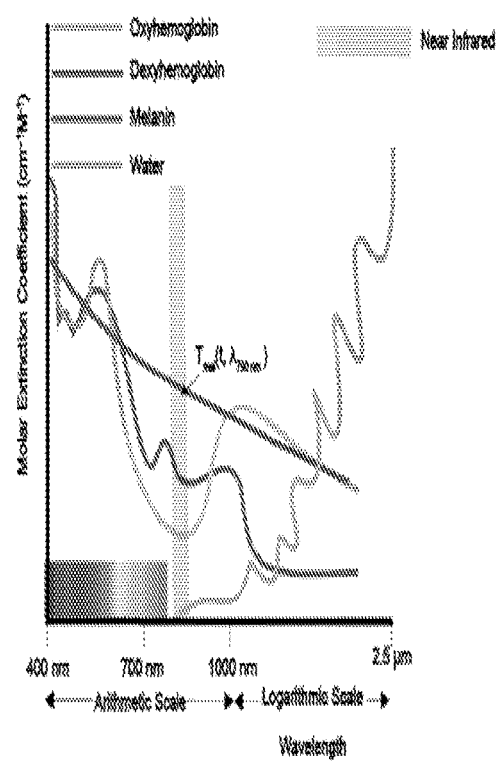
FIG. 2 is an example of a polarization-based pulse oximeter approach laid over an absorption spectra for oxyhemoglobin, deoxyhemoglobin, melanin, and water.

Recently, other or additional wavelengths have been used to try to account for differences in melanin content of different complexions. However, irrespective of the number of additional wavelengths that are used to determine the relative contributions of $HbO_2$ and Hb, it is a fact that the difference in absorption due to melanin at the probing wavelengths will always remain nonzero across the various wavelengths. The difference in absorption being non-zero prevents the contribution of melanin from being removed. In order to more accurately determine cardiovascular variability parameters in patients of all skin tones, the present disclosure illustrates methods and systems for optical determination using polarization techniques that is independent skin contributions, especially melanin. The improved approach takes two critical steps. The first is to use the polarization of light, rather than distinct wavelengths, to discriminate the relative absorption contributions of $HbO_2$ and Hb. The second is to use an inhomogeneous state of polarization of the illuminating light to simultaneously obtain the relative absorption of $HbO_2$ and Hb for the same wavelength (see graphical representation in FIG. 2). This has the effect of canceling out the absorption effect from melanin. Moreover, this approach permits the melanin contribution to cancel out for input wavelengths of any bandwidth (e.g., over the entire visible and near-infrared spectrum), such as white light, as long as the information on $HbO_2$ and Hb is obtained simultaneously over the same bandwidth.

III. Theory

A theoretical framework is provided to explain the single-shot technique to quantify $SpO_2$ values in real-time. As described below, the polarization-based approach of pulse oximetry uses a single wavelength of light and thus accounts for the wavelength dependence of melanin. Although the following describes polarized pulse oximetry using a single frequency, it should be noted that a similar approach can be taken for polarized pulse oximetry performed using a band of frequencies within the light spectrum including but not limited to that of white light. Additionally, the degree of polarization is described as being in reflectance, additionally or alternatively, if the tissue system is sufficiently thin so that the degree of polarization of the light after penetration the skin is non-zero, this polarization pulse oximetry model will also work in transmission mode.

$SpO_2$ is defined as the ratio of $HbO_2$ (oxyhemoglobin) to the sum of $HbO_2$ and Hb (deoxyhemoglobin), and can be expressed as:

$$SpO_2 = \frac{HbO_2}{HbO_2 + Hb} \times 100\%. \quad (1)$$

The incident light emitted from a light source, such as an incoherent LED or lamp, is typically randomly polarized and polarization is encoded across the wavefront. After interacting with the tissue, the reflected or transmitted response modifies the distribution of polarizations. A polarization analyzing device then selects orthogonal polarization states (e.g., linearly horizontal and vertical, linearly −45° and +45°, or left-hand circularly polarized light and right-hand). Whereby, the spatially separated polarization channels are then detected by a light-sensitive device and the electrical signals are used for $SpO_2$ extraction. Each detected signal, for example, the parallel ($I_{par}$) and perpendicular ($I_{per}$) components can be isolated from the superficial and deep layers, respectively. $I_{par}$ is given as:

$$I_{par} = I_0 T_{mel}(t, \lambda)\left(R_s + \frac{1}{2}R_d\right), \quad (2)$$

where the polarization analyzer is oriented parallel to the incident illumination $I_0$, $R_s$ represents the superficial component of the light, and $R_d$ refers to the deeply reflected light component. $T_{mel}$ acts as an absorption filter representing the absorption due to melanin on the skin's surface. In $I_{per}$, the superficial reflected light is rejected and as a result $I_{per}$ is expressed as:

$$I_{per} = I_0 T_{mel}(t, \lambda) \frac{1}{2} R_d. \tag{3}$$

A relationship analogous to (1) between the polarization intensities and $SpO_2$ can be determined by:

$$SpO_2 = \left(1 - \frac{I_{par} - I_{per}}{I_{par} + I_{per}}\right) \times 100\% \tag{4}$$

$$SpO_2 = \left(1 - \frac{I_0 T_{mel}(t, \lambda)\left(R_s + \frac{1}{2}R_d\right) - I_0 T_{mel}(t, \lambda)\frac{1}{2}R_d}{I_0 T_{mel}(t, \lambda)\left(R_s + \frac{1}{2}R_d\right) + I_0 T_{mel}(t, \lambda)\frac{1}{2}R_d}\right) \tag{5}$$

Since $T_{mel}$ has the same time and wavelength dependence in both polarization states it cancels out. Therefore:

$$SpO_2 = \left(1 - \frac{R_s}{R_d + R_s}\right) \times 100\% \tag{6}$$

$$SpO_2 = \frac{R_d}{R_d + R_s} \times 100\%. \tag{7}$$

IV. Systems

An aspect of the present disclosure can include a system 10 (FIG. 3) that can optically determine one or more cardiovascular variability parameters, such as estimated oxygen saturation ($SpO_2$), independent of melanin pigmentation in a biological tissue. Examples of cardiovascular variability parameters include an oxygen saturation value, a heart rate value, a respiratory rate value, a tissue oxygenation value, an arterial blood pressure value, a blood vessel stiffness value, a vascular assessment value, a microvascular blood flow value, a tissue viability value, a vasomotor function value, a thermoregulation value, an orthostasis value, a neurology value, or the like. Difference in melanin pigmentation from person to person can create inaccuracies in traditional devices that are calibrated only for lighter skin tones. The system 10 can use a single shot of light at a single wavelength or band of wavelengths (e.g., white light) to determine the one or more cardiovascular variability parameters in a manner that cancels out the effects of melanin. As illustrated, the system 10 can include a light delivery portion 100 and a light reception portion 200.

The light delivery portion 100 can include a delivery device 12 that can deliver a polarized light having an inhomogeneous optical polarization wavefront to biological tissue 14 and a reception device 16 that can receive the interacted polarized light that has reflected and/or transmitted from the biological tissue 14. The polarized light can intersect and interact with the biological tissue 14 in region 30 (shown in more detail in FIG. 4). The biological tissue 14 can be skin of a patient. For example, the skin can be located at a hand, a foot, a wrist, a finger, a toe, a chest, an ear, or the like.

The delivery device 12 can include a light source 18 and a polarization shaping device 20. The light source 18 can generate a light, directed or incoherent, to illuminate the biological tissue 14. The light source can include at least one of a light emitted diode, a super luminescent diode, an incoherent lamp (e.g., xenon, tungsten, halogen, or the like), a continuous wave laser, or a femtosecond laser. The polarization shaping device 20 can shape the light generated by the light source 18 into an inhomogeneous optical polarization wavefront (shown as polarized light) that interacts with the biological tissue 14. The polarization shaping device 20 can include at least one of a linear polarizer (e.g., film, wire grid, crystal, or the like), a vortex waveplate, a vector beam generating metasurface, a polarizing beam splitter, a circular polarizer, a spatial light modulator, or an interferometer.

Once the polarized light has interacted with the biological tissue 14, for example been reflected and/or transmitted by the biological tissue, then the interacted polarized light can be received by the reception device 16 of the light reception portion 200. The reception device 16 can include a polarization analyzer 22 and a detection device 24. The detection device 24 can include at least a processor 26 and a light detector 28. The polarization analyzer 22 can receive the interacted polarized light and output light comprising at least two polarization states. The polarization analyzer 22 can include at least one of a linear polarizer or a polarizing beam splitter for analyzing the interacted polarized light. The output light can be received by the light detector 28 of the detection device 24. The light detector 28 can include at least one of a charge-coupled device (CCD) camera, a CMOS camera, a photodiode, a photoconductor, a polarimeter, a photodetector, a thermal detector, a photomultiplier tube (PMT), or a balanced detector. The light detector 28 can receive the light output from the polarization analyzer 22 and output data based on that light, for example, data related to at least two polarization states of the light output by the polarization analyzer. The processor 26 can be in communication (wired or wireless) with the light detector 28 and can receive the data from the light detector. The processor 26 may be a microprocessor that include the functions of a non-transitory memory or the processor may be in communication with a non-transitory memory (not shown in FIG. 1) storing instructions for the processor to execute.

Figure 4:
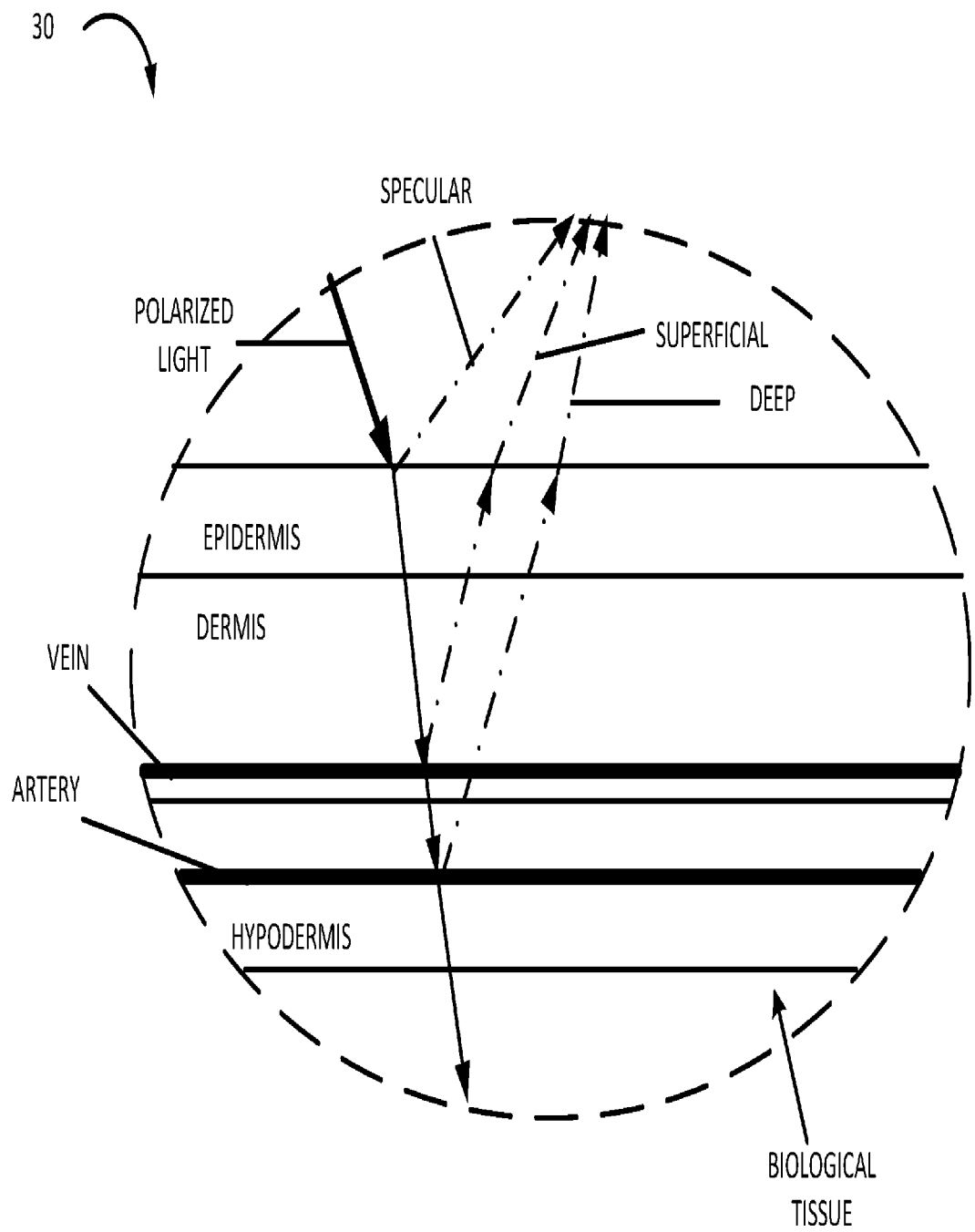
FIG. 4 is a diagram showing a zoomed in portion of FIG. 1 showing a reflection model of light interacting with skin.

FIG. 4 shows region 30 and the interaction between portions of the biological tissue 14 and the polarized light in greater detail. It should be understood that reflection is shown in FIG. 4, but transmission may occur additionally or alternatively. In FIG. 4 the biological tissue 14 is human skin of a portion of a patient's body (e.g., a finger), which can include three main layers: the epidermis, the dermis, and the hypodermis. The depth of penetration of the light can depend on the wavelength with shorter wavelengths penetrating to a shorter depth than longer wavelengths. Hemoglobin (Hb) and deoxyhemoglobin ($HbO_2$) can be found in different quantities in different regions of the skin. Generally, more Hb is found in blood vessels (e.g., veins) located in the superficial layers of skin (e.g., dermis or epidermis) and more $HbO_2$ can be found in blood vessels (e.g., arteries) located in deep layers of skin (e.g., epidermis). Light traversing through scattering media, such as biological tissue, succumbs to changes in the state-of-polarization where depolarization increases with depth of penetration.

Figure 3:
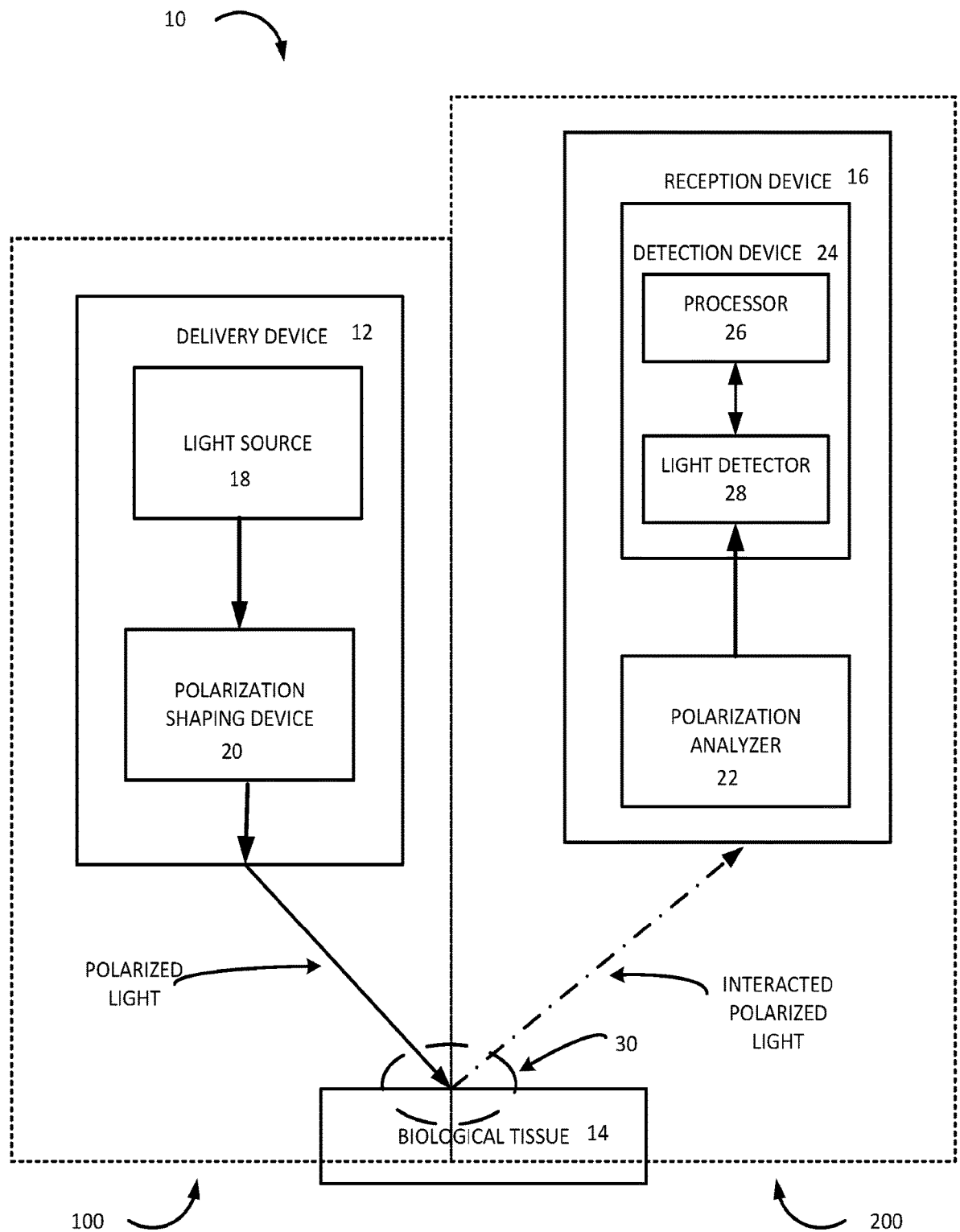
FIG. 3 is a diagram showing an example of a system that can optically determine one or more cardiovascular variability parameters independent of skin contributions using a polarization-based approach.

When the polarization shaping device 20 of FIG. 3 outputs polarized light having an inhomogeneous optical polarization wavefront toward the biological tissue 14 it first interacts with the epidermis and a specular component of light can be reflected from the epidermis. The specular component of light has a similar or the same polarization as the incident light (e.g., the polarized light) and may not be important for determining one or more cardiovascular variability parameters, such as $SpO_2$. The polarized light then interacts with the dermis, which can contain one or more veins that can include a predominantly Hb, and a superficial component of light can be reflected from the dermis and/or the at least one vein. The superficial component of light can be more depolarized than the specular component and less depolarized than a deep component. The remaining polarized light can then interact with the hypodermis, which can contain one or more arteries that can include predominantly $HbO_2$, and a deep component of light can be reflected from the hypodermis and/or the at least one artery. The deep component of light can be more depolarized than both the specular and superficial components. A portion of the polarized light may also be transmitted through the skin into other biological tissues of the patient, or out of the skin, depending on the thickness of the skin and the skin's location on the patient's body. A polarization analyzer (like polarization analyzer 22 of FIG. 3) can be positioned to receive a portion or all of the light (e.g., specular, superficial, deep, and/or transmitted) reflected by and/or transmitted from the skin.

Figure 5:
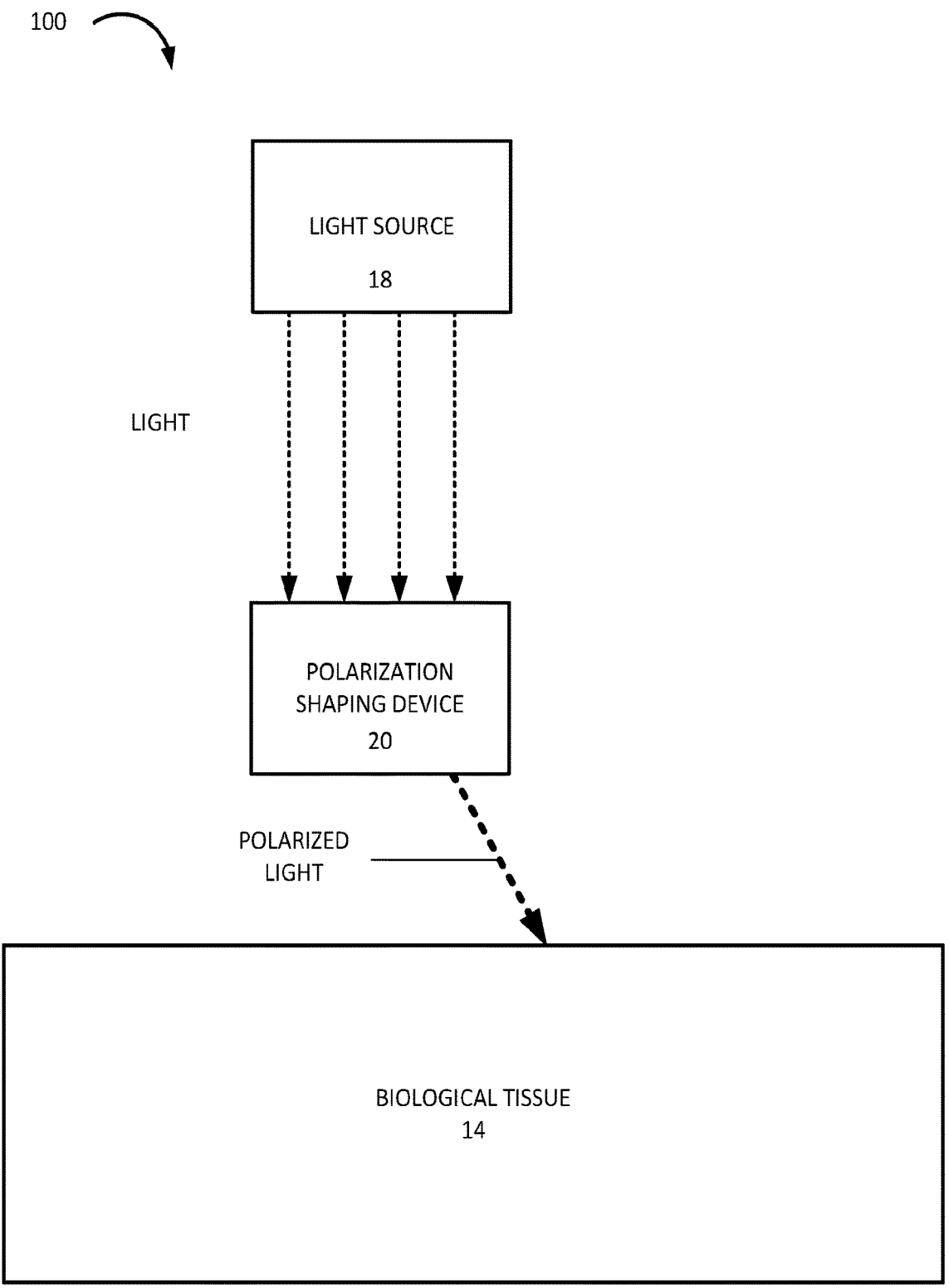
FIG. 5 is a diagram showing a portion of the system of FIG. 1 generating and polarizing light that then interacts with biological tissue.
Figure 6:
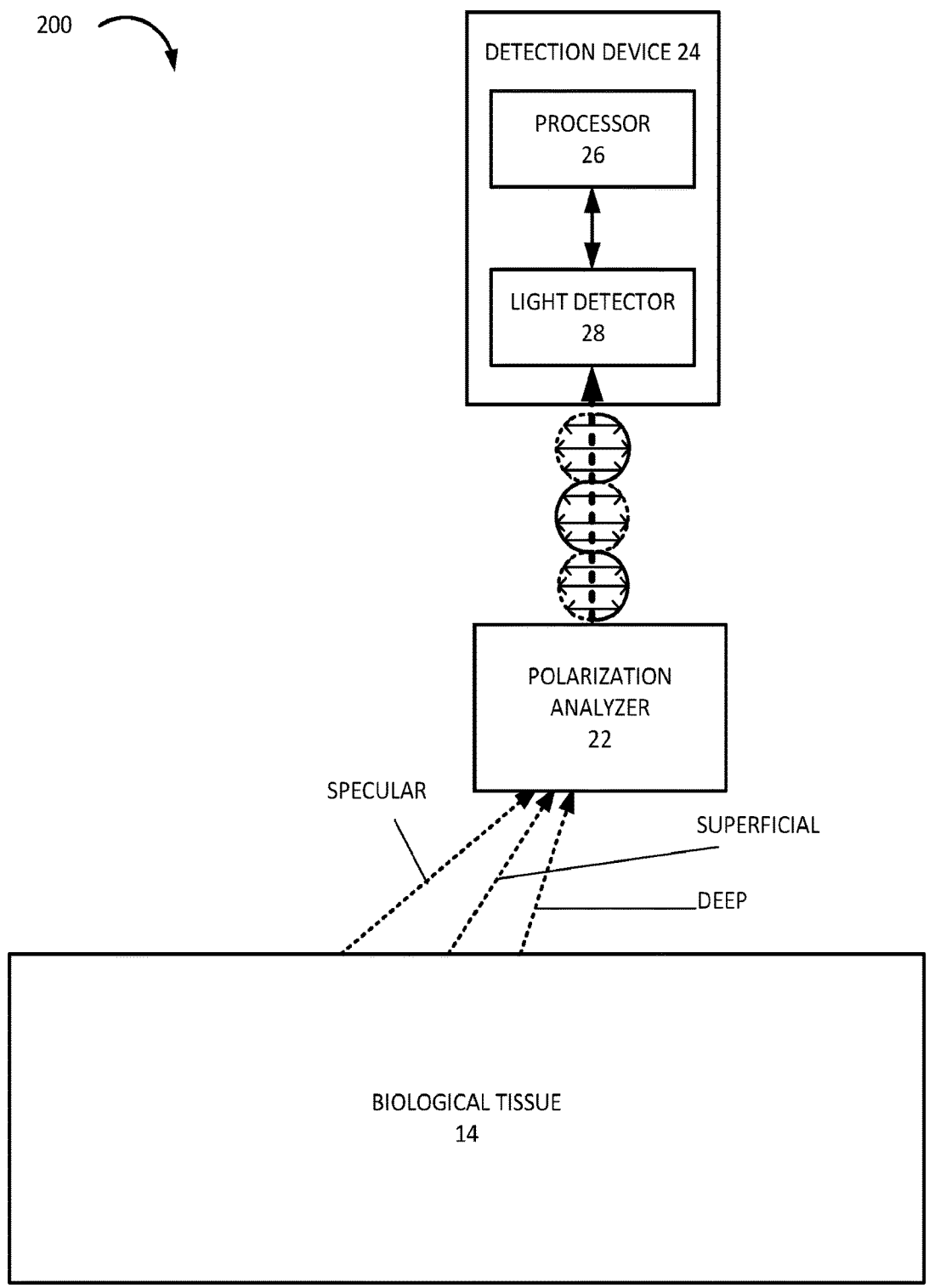
FIG. 6 is a diagram showing a portion of the system of FIG. 1 detecting and analyzing light that has been reflected from biological tissue.
Figure 7:
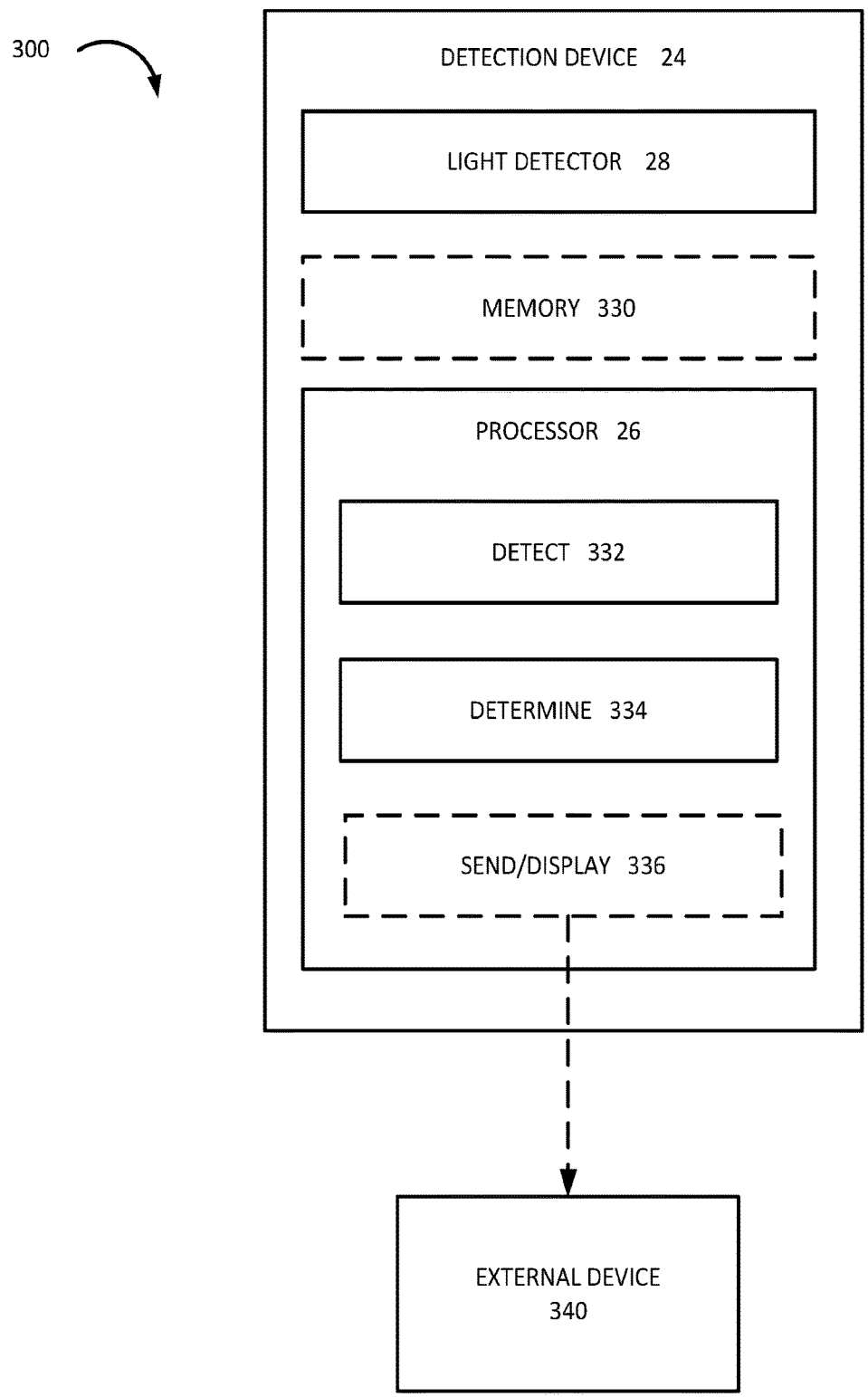
FIG. 7 is a diagram showing an example of the detection device of FIG. 1 that can interact with an external device.

FIGS. 5-7 show the components of the system 10 in greater detail. FIG. 5 shows a light delivery portion 100 of the system 10 that correlates with the delivery device in FIG. 3. The light source 18 can generate a light, directed or incoherent, to illuminate the biological tissue 14 of the patient. The light source 18 can include at least one of a light emitted diode, a super luminescent diode, an incoherent lamp (e.g., xenon, tungsten, halogen, or the like), a continuous wave laser, or a femtosecond laser. The polarization shaping device 20 can polarize the light from the light source 18 to have an inhomogeneous optical polarization wavefront creating polarized light. The polarized light can be configured to interact with the biological tissue of the patient. The interaction can be reflectance and/or transmission, as described in detail in FIG. 4. The polarization shaping device 20 can include at least one of a linear polarizer (e.g., film, wire grid, crystal, or the like), a vortex waveplate, a vector beam generating metasurface, a polarizing beam splitter, a circular polarizer, a spatial light modulator, or an interferometer. It should be understood that the angle of the polarized light incident to the biological tissue 14 must be such that the reflected and/or transmitted light can be received at the polarization analyzer 22.

FIG. 6 shows a light reception portion 200 of the system 10 that correlates with the receiving device in FIG. 3. The polarization analyzer 22 can receive the interacted polarized light, which can include the light at different stages of polarization reflected and/or transmitted after the polarized light has interacted with the biological tissue 14 of the patient. The interacted light can include at least the superficial and deep components, and may include the specular component (as shown). Light traversing through scattering media, like the biological tissue 14, succumbs to changes in the state-of-polarization where depolarization increases with depth of penetration (the depth of penetration depends on wavelength). The polarization analyzer 22 can include at least one of a linear polarizer or a polarizing beam splitter and can analyze the interacted polarized light and output at least a first polarization state and a second polarization state of the interacted polarized light. Because the interacted polarized light can include multiple polarization states based on the different depths of penetration the polarization analyzer 22 can polarize the interacted polarized light into a number of polarization states based on the type and angles of the polarizers within the polarization analyzer. The first polarization state of the interacted polarized light is represented by the dotted line sinusoidal wave with vector arrows and the second polarization state of the interacted polarized light is represented by the unbroken line sinusoidal wave with vector arrows in FIG. 6.

A portion of the polarization analyzer 22 can be oriented at a first angle relative to the interacted polarized light to output the first polarization state of the interacted polarized light. Another portion of the polarization analyzer 22 can be oriented at a second angle relative to the interacted polarized light to output the second polarization state of the interacted polarized light. The first and second polarization states of the interacted polarized light can be obtained simultaneously. The first polarization state and the second polarization states can be orthogonal to each other. In some instances, the first and second polarization states may be almost orthogonal (e.g., within 1°, 5°, 10°, 15°, 20°, 30° or the like of orthogonality. For example, the orthogonality can be one of: linearly horizontal and vertical polarization states, linearly −45° and +45° polarization states, or left-hand circularly polarized light and right-hand polarization states. The type of orthogonality can depend on the type of polarization analyzer 222. Example mathematics throughout refer to perpendicular and parallel linear polarization states but can be understood to apply to any first and second polarization states. The first and second polarization states need not be orthogonal in some instances.

The polarization analyzer 22 is in communication with a detection device 24 that can include a light detector 28 and at least a processor 26. The light detector 28 can detect the first and second polarization states of the interacted polarized light output by the polarization analyzer 22. The light detector 28 can include at least one of a charge-coupled device (CCD) camera, a CMOS camera, a photodiode, a photoconductor, a polarimeter, a photodetector, a thermal detector, a photomultiplier tube (PMT), or a balanced detector. The light detector 28 can be in communication (wired or wireless) with at least the processor 26. The processor 26 can execute instructions at least for the determination of one or more cardiovascular variability parameters using the first and second polarization states of the interacted polarized light output by the polarization analyzer 22.

As shown in FIG. 7, an example 300 of the detection device 24 is illustrated. The detection device 24 can include the light detector 28 (as described with respect to FIG. 6) and a processor 26. The detection device 24 may include a non-transitory memory (memory 330) for storing instructions that can be executed be the processor 26. In some instances, the processor 26 can be a microprocessor or other type of processor device that can itself include functionality like that of a memory feature/component for storing instructions. The processor 26 can execute instructions for detection 332, determination 334, and sending and/or displaying 336. The processor 26 may also execute other instructions not shown, but described herein. The processor can detect 332 data related to the first polarization state of the interacted polarized light and data related to the second polarization state of the interacted polarized light from the light detector 28. The processor 26 can determine 334 relative absorption contributions of a superficial component and a deep component of the biological tissue of the patient (e.g., the superficial and deep components of the light from FIGS. 4 and 6) based on the data related to the first polarization state of the interacted polarized light and the data related to the second polarization state of the interacted polarized light. The absorption contribution of the superficial component can be analogous to an absorption contribution of deoxyhemoglobin and the absorption contribution of the deep component can be analogous to an absorption contribution of oxyhemoglobin. The processor 26 can also determine 334 a cardiovascular variability parameter of the patient based on the relative absorption contributions of the superficial component and the deep component. Such a determination can be independent of an absorption effect of melanin in the biological tissue because the absorption effect of the melanin is cancelled out by analyzing polarizations state data from the single shot of light at a wavelength or a group of wavelengths instead of wavelength and/or frequency data from multiple shots of light having at least two different wavelengths. The processor 26 can also include instructions to send and/or display 336 the determined cardiovascular variability parameter. The processor 26 may display the determined cardiovascular variability parameter on a display (not shown) associated with and in communication with the system 10. The processor 26 can also send the determined cardiovascular variability parameter to an external device 340 associated with the patient and/or a medical professional.

V. Methods

Another aspect of the present disclosure can include method 400 (FIG. 8) for optically determining one or more cardiovascular variability parameters of a patient independent of the effects of melanin. Cardiovascular variability parameters can include, for example, an oxygen saturation value, a heart rate value, a respiratory rate value, a tissue oxygenation value, an arterial blood pressure value, a blood vessel stiffness value, a vascular assessment value, a microvascular blood flow value, a tissue viability value, a vasomotor function value, a thermoregulation value, an orthostasis value, or a neurology value. The method 400 can be executed using the system 10 shown in FIGS. 3-7. For purposes of simplicity, the method 400 is shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the method 400, nor is method 400 limited to the illustrated aspects.

At step 402, data related to a first polarization state and a second polarization state of an interacted polarized light can be received by a detection device that can include at least a processor and a light detector. The interacted polarized light can include polarized light reflected after a polarized light interacts with the biological tissue of the patient (e.g., skin). The detection device can also be a part of a system, such as system 10, that also includes a light source, a polarization shaping device, and a polarization analyzer. The light source can generate light to illuminate the biological tissue. The light source may be controlled manually and/or semi- or fully automatically via a controller (e.g., a PID controller). The polarization shaping device can polarize the light to have an inhomogeneous optical polarization wavefront. The polarized light can interact with the biological tissue of the patient. The interaction can be reflectance and/or transmission. The polarization analyzer can receive the interacted polarized light and output at least the first polarization state and the second polarization state of the interacted polarized light. A portion of the polarization analyzer can be oriented at a first angle relative to the interacted polarized light to output the first polarization state. Another portion of the polarization analyzer can be oriented at a second angle relative to the interacted polarized light to output the second polarization state. The first and second polarization states of the interacted light can be output simultaneously. The light detector of the detection device can detect the first and second polarization states of the light output by the polarization analyzer and then send the data related to the first and second polarization states of the light to the processor.

At step 404, the detection device can determine relative absorption contributions of a superficial component and a deep component of the biological tissue of the patient based on the data related to the first polarization state and the data related to the second polarization state. The first polarization state and the second polarization state of the interacted polarized light can be orthogonal to each other, as an example. The orthogonality can be one of: linearly horizontal and vertical polarization states, linearly −45° and +45° polarization states, or left-hand circularly polarized light and right-hand polarization states. In one example, the first polarization state of the interacted polarized light can be a parallel polarization state of the interacted polarized light and the second polarization state of the interacted polarized light can be a perpendicular polarization state of the interacted polarized light. The polarization analyzer can be oriented parallel relative to the interacted polarized light to output the parallel polarization state and perpendicular relative to the interacted polarized light to output the perpendicular polarization state.

The data related to the first polarization state can include the relative absorption contributions of the superficial component and the deep component of the biological tissue of the patient and the data related to the second polarization state can include the relative absorption contribution of the superficial component the biological tissue of the patient. For example, the relative absorption contributions of the superficial component and the deep component of the biological tissue of the patient can be determined by solving a system of equations $$I_{par} = I_0 T_{mel}(t, \lambda)\left(R_s + \frac{1}{2}R_d\right) \quad (1)$$

$$I_{per} = I_0 T_{mel}(t, \lambda)\frac{1}{2}R_d \quad (2)$$

for the relative absorption contribution of the superficial component ($R_s$) and the relative absorption contribution of the deep component ($R_d$). The data related to the first polarization state is $I_{par}$, the data related to the second polarization state is $I_{per}$, the interacted polarized light is $I_O$, and the absorption contribution of melanin is $T_{mel}$.

At step 406, the detection device can determine a cardiovascular variability parameter of the patient based on the relative absorption contributions of the superficial component and the deep component. The determination can be independent of an absorption effect of melanin in the biological tissue. For example, if the cardiovascular variability parameter being determined is estimated oxygen saturation ($SpO_2$), then the determination can include solving the equation:

$$SpO_2 = \frac{R_d}{R_d + R_s} \times 100\%. \quad (3)$$

The equation (3) can be solved with the =relative absorption contribution of the superficial component ($R_s$) and the relative absorption contribution of the deep component ($R_d$) determined in step 404. Then the relationships can be expressed as:

$$SpO_2 = \frac{HbO_2}{HbO_2 + Hb} \times 100\% \text{ and} \quad (3)$$

$$SpO_2 = \frac{R_d}{R_d + R_s} \times 100\% \quad (4)$$

Other mathematical relationships can be solved for determining other cardiovascular variability parameters.

Figure 8:
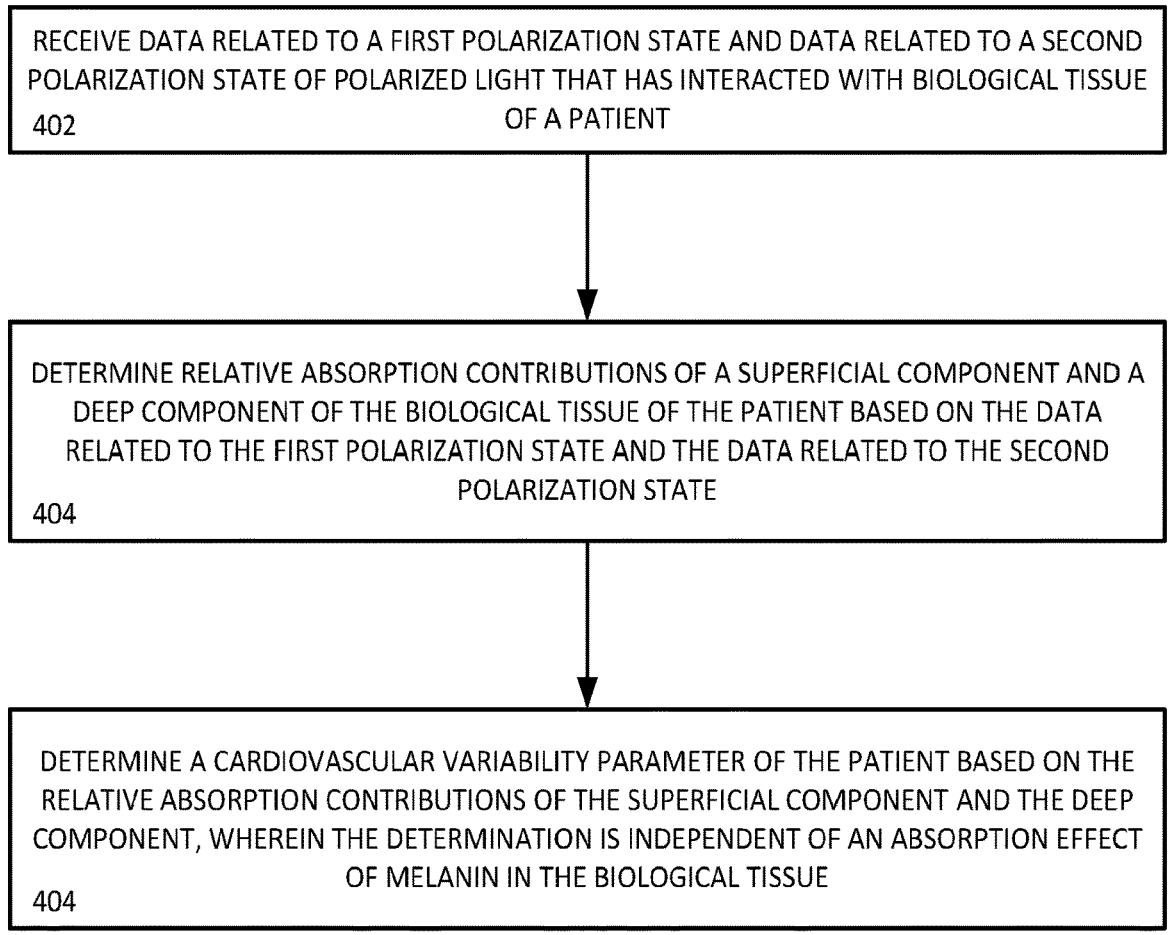
FIG. 8 is a process flow diagram of a method for optically determining one or more cardiovascular variability parameters independent of skin contributions using a polarization-based approach.

While not shown in FIG. 8, the detection device can also output, via a transceiver of the detection device, the cardiovascular variability parameter to an external device (e.g., a smart phone, a computer, a tablet, a clinical base station, or the like) associated with the patient and/or a medical professional. In some instances, the system, including the detection device, can also determine a health state of the patient based on a trend of the determined cardiovascular parameter over a period of time. and output a notification of the health state of the patient to the external device associated with the patient and/or a medical professional.

VI. Experimental

The following experiment shows the first demonstration of pulse oximetry to estimate oxygen saturation ($SpO_2$) carried out using a radially polarized vector beam using single-shot data acquisition at a single wavelength. Notably, the pulse oximetry can be conducted to estimate $SpO_2$ independent of the skin tone (melanin) and other light absorbing components of skin.

Methods
Incoherent Vector Field Generation and Characterization

Figure 9:
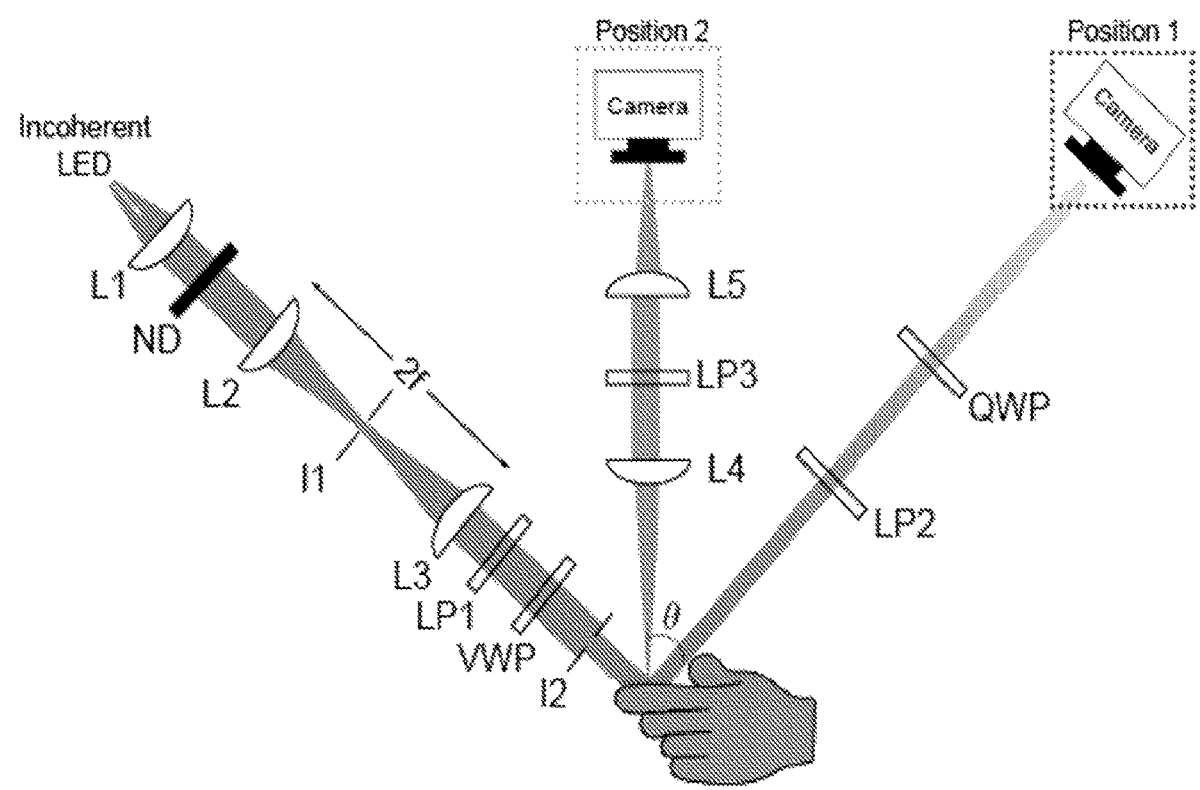
FIG. 9 is a schematic showing experimental and calibration set-up.

The combined experimental and calibration setup system for an example of the system described herein, referred to as RPOX, is shown in FIG. 9. An LED light source (Thorlabs M780L3-C1) spectrally centered at 780-nm wavelength, where tissue absorption is low, is first collimated by a lens (L1) and then impinges on a neutral density (ND) filter, which attenuates the power to 431 ρW. Next, a spatial filtering system comprising an aspheric lens (L2), iris (I1), and collimating lens (L3) arranged in a 2f system generates an aberration-free, circularly symmetric beam. A linear polarizer (LP1) is subsequently used to ensure that vertically polarized light propagates through a zero-order vortex wave plate (Thorlabs WPV10L-780) for radially polarized vector field generation. For calibration, a silvered mirror (not shown) is used to direct the vector field to a CMOS camera (EO2122M) located at position 1, as indicated in FIG. 9. Conversely, the camera is moved to position 2 when $SpO_2$ measurements are carried out, and the mirror is replaced by the individual's finger.

Figure 10:
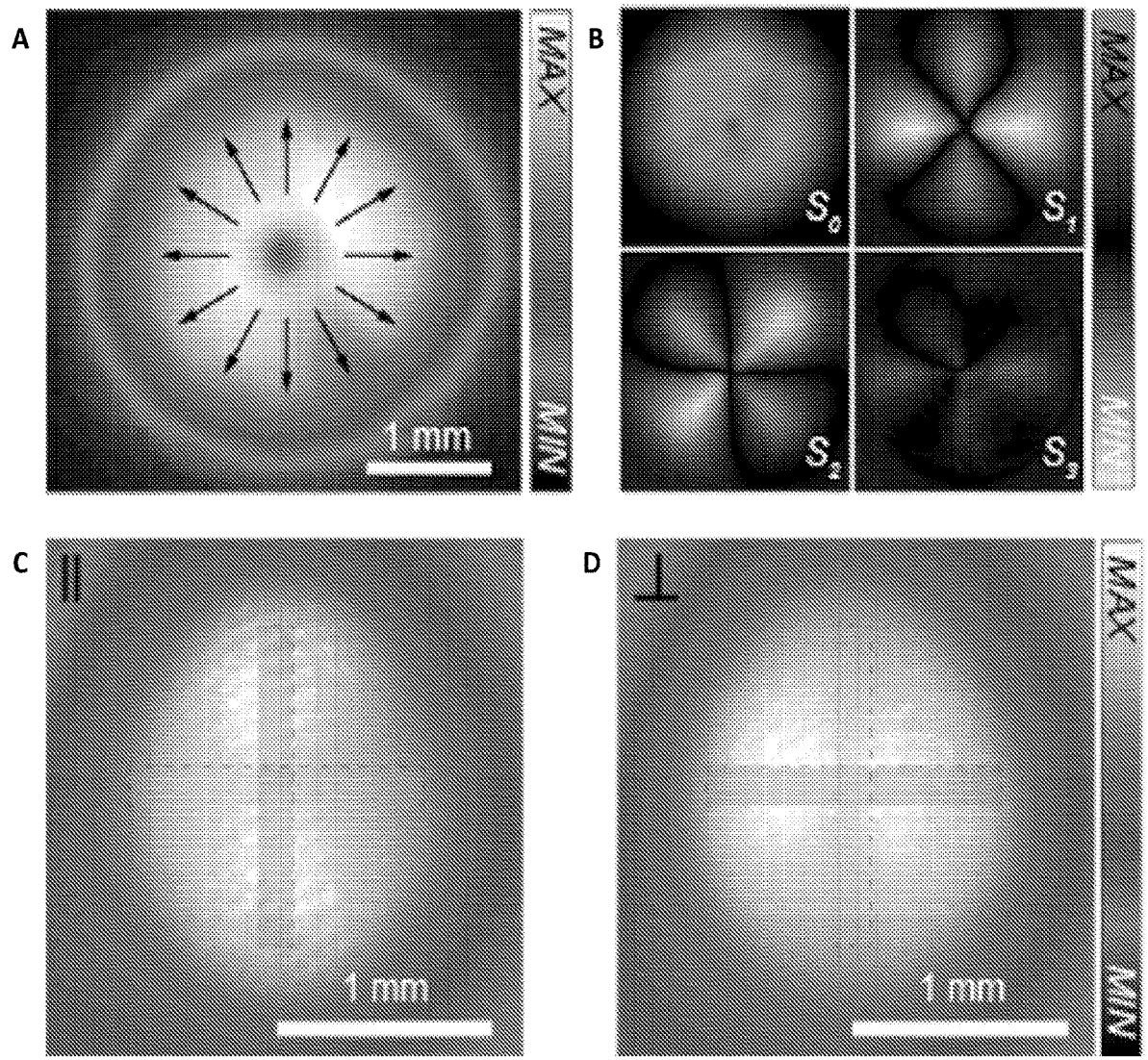
FIG. 10 shows photographic representations of radial vector beams of states of polarization of the light (element A), stokes parameters of the light (element B), and intensity vector distributions generated after the light beam has passed through a polarization analyzer oriented parallel (element C) and perpendicular (element D) to the direction of the light.

The radially polarized vector beam from an incoherent source is first calibrated. The Stokes parameters of the vector field were measured by inserting polarization analyzer LP2 and a quarter-wave plate (QWP) into the beam path immediately preceding the camera, as shown in FIG. 9. The relative intensity contributions of the various polarization components to the SoP of the vector field are then determined by the Stokes parameters defined as $$S_0 = I_H + I_V,\ S_1 = I_H - I_V,\ S_2 = I_{D+} - I_{D-},\ S_3 = I_{RCP} - I_{LCP} \quad (15)$$

where $I_H$, $I_V$, $I_{D+/-}$, $I_{LCP}$, and $I_{RCP}$ are the intensities of the horizontal and vertical, two diagonals, and left/right circular polarization states, respectively. In FIG. 10, element A the black arrows indicate the direction of the local electric field, while FIG. 10, element B displays the experimentally obtained corresponding Stokes parameters. the typical doughnut-shaped intensity distribution with a polarization singularity in the center and Stokes parameters that correspond to a radially polarized vector field were observed.

Data Collection Procedure

Prior to carrying out measurements, informed consent is given by the volunteers. At this time, the volunteers are asked to fill a survey that collects information regarding their level of physical activity, caffeine consumption, smoking habits, and whether they are wearing nail-polish. This data set consists of five healthy volunteers of varying skin tones, (I-VI on the Fitzpatrick scale. Of these 5 volunteers aged between 23 and 34 years, 3 are males and 2 females. Two trials per individual are carried out in a dark room at 65° F. ambient temperature, each trial being 2 hours apart to account for intrapersonal variations. At the time of the study, volunteers are required to wear a face mask over their nose and mouth in order to comply with Brown University COVID policy. After 10 minutes of acclimatization to the lab environment, volunteers are asked to breathe under normal, deep, held, and shallow breathing conditions, which are synchronized by an audible metronome for 160 seconds. Normal breathing conditions entail volunteers breathing at a rate of 17 breaths per minute while deep breathing entails a rate of 6 breaths per minute. This is followed by breathing at a rate of 17 breaths per minute, occurring after the volunteer have held their breath for 30 seconds. Finally, the volunteers are asked to perform shallow breathing at 30 breaths per minute. Note that for this study, a waiver for IRB approval was received because the work focuses on calibrating the device, and thus does not meet the federal definition of generalizability.

Vector-Beam Pulse Oximetry

As shown in FIG. 9 volunteers insert their finger into the optical setup after the generation of the vector beam where an iris (I2) is used to aperture the size of the beam. The non-specular light reflected from the deep and diffuse layers of the finger is collected by a 4f system comprising lenses L4 (focal length=30 mm) and L5 (focal length=30 mm), and subsequently imaged onto the camera at position 2. A linear polarization analyzer LP3 is placed after the finger and is set to be parallel to the illumination polarization produced by LP1. A series of 8000 frames is collected at 50 frames per second, where FIG. 10, element C and FIG. 10, element D depict typical intensity profiles when LP3 is oriented parallel and perpendicular to LP1, respectively. These frames are then processed in MATLAB to generate the regions of interest as depicted by the horizontal and vertical boxes in FIG. 10, element C and FIG. 10, element D. This experiment makes use of FIG. 10, element C. The vertical box represents $I_{par}$ and the horizontal box represents $I_{per}$. Eq. (1-4) are then applied to calculate $SpO_2$ for RPOX, where the $SpO_2$ value is averaged across 8000 frames. In tandem, two commercial pulse oximeters (Metene JPD500D and Masimo MightySat) are attached to a volunteer's middle and index finger, respectively, on the right hand, where reference $SpO_2$ measurements are recorded. Each commercial pulse oximeter has a reported accuracy of 2%.

Statistical Methods

Participant-level characteristics are summarized with descriptive statistics. The main objective is to evaluate the performance of RPOX compared to the Metene and Masimo pulse oximeters. A linear regression model is used which regresses $SpO_2$ on device type (effect-coded to allow for pairwise comparisons between RPOX vs. Metene and RPOX vs. Masimo), controlling for confounders identified apriori. Interest was in estimating effect sizes and confidence intervals, rather than strict statistical hypothesis testing. Data was analyzed using R statistical software.

Results

As shown in Table 1, t results suggest no significant difference in mean $SpO_2$ between the Masimo oximeter and RPOX (p=0.2078) as well as between the Metene oximeter and RPOX (with p=0.0918) as summarized by the multiple linear regressions analysis shown in Table 1.

TABLE 1

| Variable | Estimated Coefficient | Coefficient Standard Error | t value | Pr (>\|t\|) | P-value summary |
|---|---|---|---|---|---|
| Intercept | 96.7851 | 0.5476 | 164.716 | $<2 \times 10^{-16}$ | *** |
| Masimo | 1.1063 | 0.8310 | 1.331 | 0.2078 | |
| Metene | 1.5228 | 0.8310 | 1.833 | 0.0918 | |

Unadjusted outcomes are summarized in Table 2 across breathing conditions and participants. Participant outcomes are collapsed within individuals across conditions. From Table 2 RPOX is noted to have the lowest standard deviation (SD) for each volunteer ($1.21 \times 10^{-4}$ for participant 1, $4.15 \times 10^{-6}$ for participant 2, $3.23 \times 10^{-6}$ for participant 3, $5.26 \times 10^{-6}$ for participant 4 and $3.0 \times 10^{-6}$ for participant 5) indicating that the measurements taken by RPOX are the most consistent when considering each participant separately.

TABLE 2

| Participant | Device | Mean (%) | Standard deviation |
|---|---|---|---|
| 1 | RPOX | 94.1 | $1.21 \times 10^{-4}$ |
| | Masimo | 99.2 | $3.42 \times 10^{-1}$ |
| | Metene | 98.3 | 1.29 |
| 2 | RPOX | 98.2 | $4.15 \times 10^{-6}$ |
| | Masimo | 98.7 | $3.35 \times 10^{-1}$ |
| | Metene | 99.3 | $2.58 \times 10^{-1}$ |
| 3 | RPOX | 96.8 | $3.23 \times 10^{-6}$ |
| | Masimo | 97.3 | $2.29 \times 10^{-1}$ |
| | Metene | 96.7 | $3.01 \times 10^{-1}$ |
| 4 | RPOX | 97.8 | $5.26 \times 10^{-6}$ |
| | Masimo | 98.2 | $3.09 \times 10^{-1}$ |
| | Metene | 98.3 | $3.62 \times 10^{-1}$ |
| 5 | RPOX | 97.0 | $3.0 \times 10^{-6}$ |
| | Masimo | 96.0 | $3.34 \times 10^{-1}$ |
| | Metene | 99.9 | $1.29 \times 10^{-1}$ |

Figure 11:
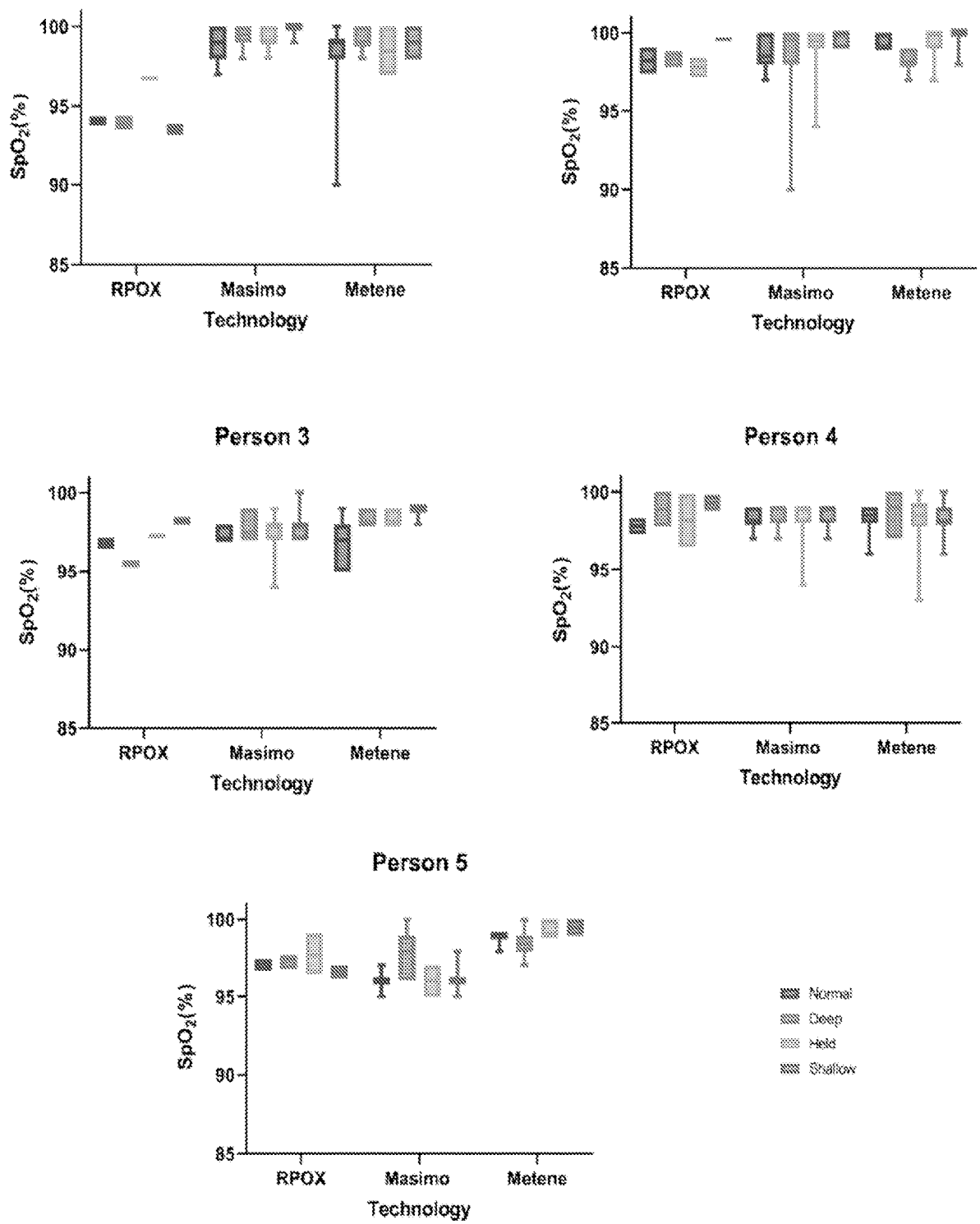
FIG. 11 shows box and whisker plots for 5 participants under normal, deep, held, and shallow breathing conditions.

FIG. 11 shows box and whisker plots of the results obtained for each participant under four different breathing conditions (shown by four different colors) for each device. It is observed that RPOX provides oxygen saturation levels close to a baseline defined by the commercial devices for the normal, deep, held, and shallow breathing cases. The highest mean $SpO_2$ value recorded for RPOX and Masimo for person 2, 3 and 4 was recorded under shallow breathing conditions. According to FIG. 11 the Masimo and Metene prior art standard devices are more likely to record large variation in the $SpO_2$ measurements collected over 160 seconds as shown by the range of values in the box and whisker plots. The value for participant 1 is below the expected range for healthy patients (95-100%) for the normal, deep, and shallow breathing conditions.

Figure 12:
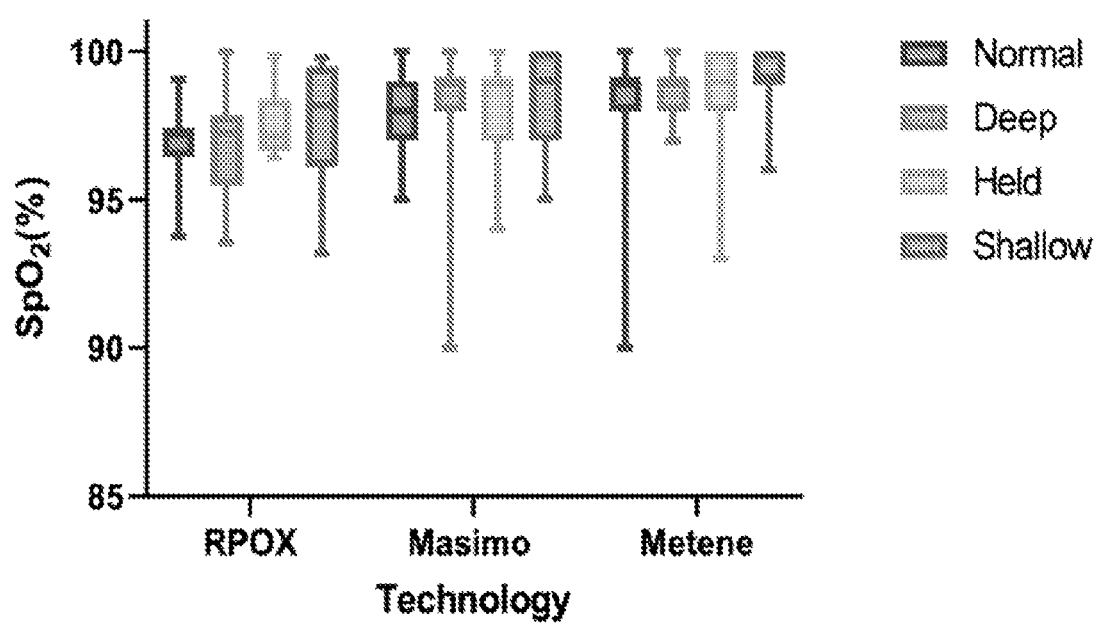
FIG. 12 shows average $SpO_2$ values comparing the device described herein to traditional devices under various breathing conditions.

FIG. 12 depicts the combined-data box and whisker plots across participants for each device while the mean and standard deviation values for this data are summarized in Table 3. The purpose of combining the participant data is to evaluate the overall performance of RPOX when compared to Masimo and Metene. It is evident from Table 3 that RPOX shows the most variation for all breathing conditions except that of the held breathing condition, where RPOX shows the least variation. RPOX shows the most variation under shallow breathing condition (2.26%). From FIG. 12 and Table 3, it is noted that the $SpO_2$ readings recorded by RPOX are (0.4-0.9%) lower than those recorded by Masimo and Metene. Additionally, RPOX shows the largest interquartile range in measured $SpO_2$ values under the deep, held, and shallow breathing conditions in person 4.

TABLE 3

| Breathing Condition | Device | Mean (%) | Standard deviation |
|---|---|---|---|
| Normal | RPOX | 96.2 | 1.55 |
| | Masimo | 97.7 | 1.37 |
| | Metene | 97.7 | 1.50 |
| Deep | RPOX | 96.2 | 1.93 |
| | Masimo | 97.9 | 1.39 |
| | Metene | 98.0 | 0.969 |
| Held | RPOX | 97.0 | 1.12 |
| | Masimo | 97.5 | 1.56 |
| | Metene | 98.2 | 1.22 |
| Shallow | RPOX | 96.9 | 2.26 |
| | Masimo | 97.5 | 1.50 |
| | Metene | 98.2 | 0.841 |

To investigate the influence of the data obtained for participant 1 on the combined participant data across devices, participant 1 is omitted from the data set summarized in Table 4. Consequently, RPOX shows the least variation in the normal and held breathing conditions.

TABLE 4

| Device | Breathing Condition | Mean (%) | Standard deviation |
|---|---|---|---|
| Normal | RPOX | 96.8 | 1.26 |
| | Masimo | 97.9 | 1.49 |
| | Metene | 98.1 | 1.59 |
| Deep | RPOX | 96.8 | 1.84 |
| | Masimo | 98.6 | 1.32 |
| | Metene | 98.4 | 0.935 |
| Held | RPOX | 97.5 | 1.17 |
| | Masimo | 98.0 | 1.62 |
| | Metene | 98.6 | 1.24 |
| Shallow | RPOX | 97.6 | 2.05 |
| | Masimo | 98.1 | 1.54 |
| | Metene | 99.0 | 0.828 |

From the above description, those skilled in the art will perceive improvements, changes, and modifications. Such improvements, changes and modifications are within the skill of one in the art and are intended to be covered by the appended claims.

The following is claimed:

1. A system comprising:
   a light source configured to generate a light to illuminate a biological tissue of a patient;
   a polarization shaping device configured to polarize the light to have an inhomogeneous optical polarization wavefront creating polarized light, wherein the polarized light is configured to interact with the biological tissue of the patient, wherein the interaction is reflectance and/or transmission;

a polarization analyzer configured to:
receive interacted polarized light comprising the polarized light reflected after the polarized light interacts the biological tissue of the patient; and
output at least a first polarization state and a second polarization state of the interacted polarized light,
wherein a portion of the polarization analyzer is oriented at a first angle relative to the interacted polarized light to output the first polarization state and another portion of the polarization analyzer is oriented at a second angle relative to the interacted polarized light to output the second polarization state; and a detection device comprising:
a light detector configured to detect the first and second polarization states of the interacted polarized light output by the polarization analyzer, and
at least a processor configured to execute instructions to:
detect data related to the first polarization state of the interacted polarized light and data related to the second polarization state of the interacted polarized light;
determine relative absorption contributions of a superficial component and a deep component of the biological tissue of the patient based on the data related to the first polarization state of the interacted polarized light and the data related to the second polarization state of the interacted polarized light; and
determine a cardiovascular variability parameter of the patient based on the relative absorption contributions of the superficial component and the deep component, wherein the determination is independent of an absorption effect of melanin in the biological tissue.

2. The system of claim 1, wherein the processor is further configured to send the cardiovascular variability parameter to an external device associated with the patient and/or a medical professional.

3. The system of claim 1, wherein the light detector comprises at least one of a charge-coupled device (CCD) camera, a CMOS camera, a photodiode, a photoconductor, a polarimeter, a photodetector, a thermal detector, a photomultiplier tube (PMT), or a balanced detector.

4. The system of claim 1, wherein the polarization analyzer further comprises at least one of a linear polarizer or a polarizing beam splitter.

5. The system of claim 1, wherein the polarization shaping device comprises at least one of a linear polarizer, a vortex waveplate, a vector beam generating metasurface, a polarizing beam splitter, a circular polarizer, a spatial light modulator, or an interferometer.

6. The system of claim 1, wherein the light source comprises at least one of a light emitted diode, a super luminescent diode, an incoherent lamp, a continuous wave laser, or a femtosecond laser.

7. The system of claim 1, wherein the biological tissue is skin, wherein the skin is located at a hand, a foot, a wrist, a finger, a chest, or an ear of the patient.

8. The system of claim 1, wherein the absorption contribution of the superficial component is analogous to an absorption contribution of deoxyhemoglobin and the absorption contribution of the deep component is analogous to an absorption contribution of oxyhemoglobin.

9. The system of claim 1, wherein the first polarization state and the second polarization state are orthogonal to each other, wherein the orthogonality is one of: linearly horizontal and vertical polarization states, linearly −45° and +45° polarization states, or left-hand circularly polarized light and right-hand polarization states.

10. The system of claim 1, wherein the cardiovascular variability parameter comprises an oxygen saturation value, a heart rate value, a respiratory rate value, a tissue oxygenation value, an arterial blood pressure value, a blood vessel stiffness value, a vascular assessment value, a microvascular blood flow value, a tissue viability value, a vasomotor function value, a thermoregulation value, an orthostasis value, or a neurology value.

11. A method comprising:
receiving, by a detection device comprising at least a processor and a light detector, data related to a first polarization state and a second polarization state of an interacted polarized light, wherein the interacted polarized light comprises polarized light reflected after a polarized light interacts with biological tissue of a patient, wherein the detection device is part of a system that further comprises:
a light source configured to generate light to illuminate a biological tissue of a patient;
a polarization shaping device configured to polarize the light to have an inhomogeneous optical polarization wavefront, wherein the polarized light is configured to interact with the biological tissue of the patient wherein the interaction is reflectance or reflectance and transmission; and
a polarization analyzer configured to receive the interacted polarized light and output at least the first polarization state and the second polarization state of the interacted polarized light, wherein a portion of the polarization analyzer is oriented at a first angle relative to the interacted polarized light to output the first polarization state and another portion of the polarization analyzer is oriented at a second angle relative to the interacted polarized light to output the second polarization state,
wherein the light detector of the detection device is configured to detect the first and second polarization states of the light output by the polarization analyzer;
determining, by the detection device, relative absorption contributions of a superficial component and a deep component of the biological tissue of the patient based on the data related to the first polarization state and the data related to the second polarization state; and
determining, by the detection device, a cardiovascular variability parameter of the patient based on the relative absorption contributions of the superficial component and the deep component, wherein the determination is independent of an absorption effect of melanin in the biological tissue.

12. The method of claim 1, further comprising outputting, by a transceiver of the detection device, the cardiovascular variability parameter to an external device associated with the patient and/or a medical professional.

13. The method of claim 11, wherein the cardiovascular variability parameter comprises an oxygen saturation value, a heart rate value, a respiratory rate value, a tissue oxygenation value, an arterial blood pressure value, a blood vessel stiffness value, a vascular assessment value, a microvascular blood flow value, a tissue viability value, a vasomotor function value, a thermoregulation value, an orthostasis value, or a neurology value.

14. The method of claim 11, wherein the first polarization state and the second polarization state of the interacted polarized light are orthogonal to each other, wherein the orthogonality is one of: linearly horizontal and vertical polarization states, linearly −45° and +45° polarization states, or left-hand circularly polarized light and right-hand polarization states.

15. The method of claim 14, wherein the first polarization state of the interacted polarized light is a parallel polarization state of the interacted polarized light and the second polarization state of the interacted polarized light is a perpendicular polarization state of the interacted polarized light,
wherein the polarization analyzer is oriented parallel relative to the interacted polarized light to output the parallel polarization state and perpendicular relative to the interacted polarized light to output the perpendicular polarization state.

16. The method of claim 11, wherein the data related to the first polarization state comprises the relative absorption contributions of the superficial component and the deep component of the biological tissue of the patient and the data related to the second polarization state comprises the relative absorption contribution of the superficial component the biological tissue of the patient.

17. The method of claim 16, wherein the determining the relative absorption contributions of the superficial component and the deep component of the biological tissue of the patient further comprises solving a system of equations (1) $I_{par}=I_0 T_{mel}(t,\lambda)(R_s+\frac{1}{2}R_d)$ and (2) $I_{per}=I_0 T_{mel}(t,\lambda)\frac{1}{2}R_d$ for the relative absorption contribution of the superficial component ($R_s$) and the relative absorption contribution of the deep component ($R_d$), wherein the data related to the first polarization state is $I_{par}$, the data related to the second polarization state is $I_{per}$, the interacted polarized light is $I_O$, and the absorption contribution of melanin is $T_{mel}$.

18. The method of claim 11, wherein the determining the cardiovascular variability parameter further comprises determining an estimated oxygen saturation ($SpO_2$) based on solving $$SpO_2 = \frac{R_d}{R_d + R_s} \times 100\%.$$

19. The method of claim 11, wherein the absorption contribution of the superficial component is analogous to an absorption contribution of deoxyhemoglobin and the absorption contribution of the deep component is analogous to an absorption contribution of oxyhemoglobin.

20. The method of claim 11, wherein the method further comprises:
determining, by the system, a health state of the patient based on a trend of the determined cardiovascular parameter over a period of time; and
outputting, by the system, a notification of the health state of the patient to an external device associated with the patient and/or a medical professional.

* * * * *